United States Patent [19]
Sechrist et al.

[11] Patent Number: 5,962,761
[45] Date of Patent: Oct. 5, 1999

[54] PROCESS FOR LINEAR ALPHA-OLEFIN PRODUCTION

[75] Inventors: Paul A. Sechrist, Des Plaines; Brian H. Johnson, Long Grove, both of Ill.

[73] Assignee: Uop LLC, Des Plaines, Ill.

[21] Appl. No.: 09/173,365

[22] Filed: Oct. 15, 1998

Related U.S. Application Data

[63] Continuation-in-part of application No. 08/855,353, May 13, 1997, abandoned
[60] Provisional application No. 60/019,685, Jun. 10, 1996.
[51] Int. Cl.⁶ .............................. C07C 2/02; C07C 2/24; B01D 3/34
[52] U.S. Cl. .................... 585/530; 585/513; 585/514; 585/515; 585/523; 585/526; 585/527; 585/524; 203/49
[58] Field of Search ..................... 585/513, 514, 585/515, 523, 526, 527, 524, 530; 203/49

[56] References Cited

U.S. PATENT DOCUMENTS

| | | | |
|---|---|---|---|
| 2,391,576 | 12/1945 | Katz et al. | 196/73 |
| 4,668,823 | 5/1987 | Murray | 568/17 |
| 4,689,437 | 8/1987 | Murray | 585/526 |
| 4,716,138 | 12/1987 | Murray | 502/117 |
| 4,795,854 | 6/1989 | Levresse | 585/800 |
| 4,822,915 | 4/1989 | Murray | 568/13 |
| 5,523,508 | 6/1996 | Krawczyk et al. | 585/523 |

*Primary Examiner*—Walter D. Griffin
*Assistant Examiner*—Thuan D. Dang
*Attorney, Agent, or Firm*—Thomas K. Mcbride; John G Tolomei; John G. Cutts, Jr.

[57] ABSTRACT

A process for the continuous oligomerization of ethylene to produce linear alpha olefins by oligomerizing ethylene in a polar phase comprising a solution of transition metal catalyst system at oligomerization conditions including a temperature and pressure greater than the critical temperature and pressure of ethylene. The resulting hydrocarbon phase containing oligomers and unreacted ethylene is subjected to physical treatment which tends to render the ethylene a nonsolvent for oligomers and thereby produce a liquid stream rich in unreacted ethylene which may be recycled to the oligomerization reaction zone by pumping.

12 Claims, 1 Drawing Sheet

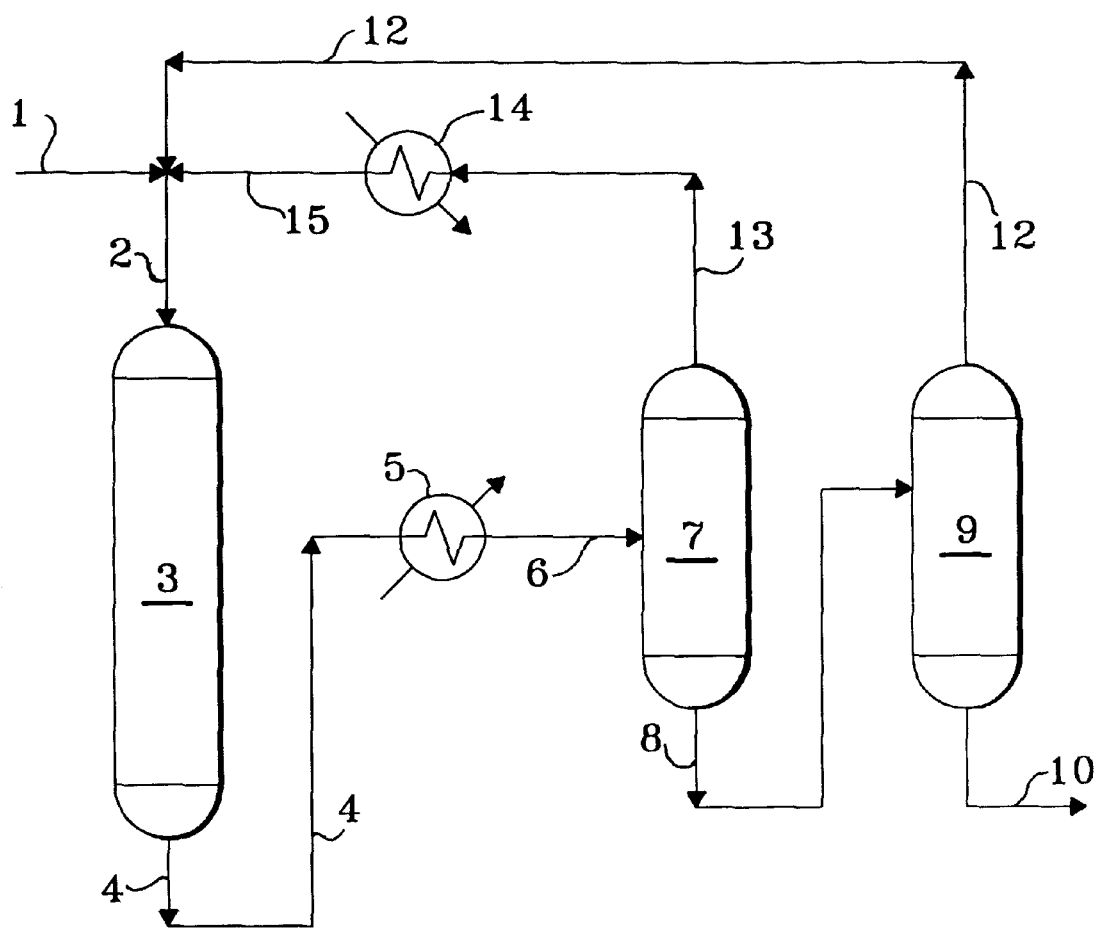

PROCESS FOR LINEAR ALPHA-OLEFIN PRODUCTION

CROSS REFERENCE TO RELATED APPLICATION

The present application is a continuation-in-part application of U.S. application Ser. No. 08/855,353 filed on May 13, 1997, now abandoned, which is a conversion of provisional application No. 60/019,685 filed on Jun. 10, 1996.

BACKGROUND OF THE INVENTION

Linear olefins are one of the most useful classes of hydrocarbons used as raw materials in the petrochemical industry and among these the linear alpha-olefins—unbranched olefins whose double bond is located at a terminus of the chain—form an important subclass. Linear alpha-olefins can be converted to linear primary alcohols by hydroformylation (oxo synthesis); alcohols of carbon number less than eleven are used in the synthesis of plasticizers whereas those of carbon number greater than eleven are used in the synthesis of detergents. Hydroformylation also can be used to prepare aldehydes as the major products which in turn can be oxidized to afford synthetic fatty acids, especially those with an odd carbon number, useful in the production of lubricants. Linear alpha-olefins also are used in the most important class of detergents for domestic use, namely, the linear alkylbenzenesulfonates, which are prepared by Friedel-Crafts reaction of benzene with linear olefins followed by sulfonation.

Another important utilization of alpha-olefins is radical hydrobromination to give primary bromoalkanes which are important intermediates in the production of thiols, amines, amine oxides and ammonium compounds. Direct sulfonation of the alpha-olefins afford the alpha-olefin sulfonates, a mixture of isomeric alkenesulfonic acids and alkanesulfones, which are effective laundry agents even in hard water and at low concentrations. Linear alpha-olefins, particularly those of eight carbons and under also are used as comonomers in the production of high density polyethylene and linear low density polyethylene.

Although linear olefins are the product of dehydrogenation of linear alkanes, the major portion of such products are the internal olefins. Preparation of alpha-olefins is based largely on oligomerization of ethylene, which has as a corollary that the alpha-olefins produced have an even number of carbon atoms. Oligomerization processes for ethylene are based mainly on organoaluminum compounds or transition metals as catalyst. Using catalytic quantities of, for example, triethylaluminum, the oligomerization of ethylene proceeds at temperatures under 200° C. to afford a mixture of alpha-olefins whose carbon number follows a Schultz-Flory distribution. In the $C_6$–$C_{10}$ range there is less than 4% branched alpha-olefins, but the degree of branching increases to about 8% as the chain length is extended to about 18. A modified process, the so-called Ethyl process, affords a high conversion of ethylene to alpha-olefins with a more controlled distribution but product quality suffers dramatically, particularly in the content of branched olefins. Thus, in the $C_{14}$–$C_{16}$ range linear alpha-olefins represent only about 76% of the product.

A notable advance in the art accompanied the use of transition metals as catalysts for ethylene oligomerization. The use of, for example, nickel, cobalt, titanium, or zirconium catalysts afforded virtually 100% monoolefins with greater than 97% as alpha-olefins, under 2.5% as branched olefins, and under 2.5% as internal olefins. Since the catalysts are insoluble in hydrocarbons, oligomerization by catalyst systems based on transition metals typically is performed in a polar solvent to solubilize the catalyst. Ethylene and its oligomers have limited solubility in the polar solvents used, which permits a continuous oligomerization process, since ethylene can be introduced into the polar phase and oligomerization products can be withdrawn as the hydrocarbon phase.

Ethylene oligomerization affords alpha-olefins with a Schultz-Flory distribution which is catalyst dependent and, at least for the catalysts of major interest herein, temperature dependent to only a minor degree. A class of catalysts having a transition metal component particularly attractive as oligomerization catalysts is described in U.S. Pat. Nos. 4,689,437, 4,716,138, 4,822,915 and 4,668,8323. Using such catalysts under conditions where the Schultz-Flory distribution constant is about 0.65 affords an oligomerization product whose alpha-olefin distribution in the $C_8$–$C_{16}$ range is particularly desirable from an economic viewpoint. That is, the economic value of ethylene oligomers may be maximized by having a Schultz-Flory distribution of about 0.65. At these operating conditions, the oligomerized reactor effluent contains oligomer compounds as well as unreacted ethylene. This unreacted ethylene must be recovered and recycled to the reaction zone. Previously, the unreacted ethylene was recovered via fractionation and then compressed before recycle to the reaction zone. Since compression is expensive, it is desirable to introduce at least a portion of recycle into the reaction zone without the necessity of compression. In accordance with the present invention, this desirable goal is achieved.

It has been discovered that the separation and recycle of supercritical ethylene can substantially reduce the amount of compression required for unconverted ethylene. Preferably, up to 90% of the ethylene can be recovered from the reactor effluent at supercritical conditions and then recycled to the reactor inlet by pumping rather than by compression. Since the supercritical separation at preferred operating conditions is not a sharp, perfect separation, about 15–25 mol % of the material recovered and recycled to the reactor are oligomers. However, one advantage to this resulting separation is that these oligomers may be used to aid in solubilizing heavy wax buildup in the reaction zone.

During the oligomerization reaction about 10% of the oligomers have 20 or more carbon atoms ($C_{20+}$) which are solids at ambient temperature. The $C_{20+}$ oligomers have limited solubility in the resulting hydrocarbon phase of the oligomerization process described above and therefore form a separate solid waxy phase. The oligomerization process then becomes a four-phase system; a vapor phase of ethylene, a polar solvent phase with dissolved catalyst, an immiscible liquid hydrocarbon phase and a solid phase of $C_{20+}$ hydrocarbons. The formation of solids tends to plug the reactor as currently configured, so a continuous process becomes interrupted periodically due to the necessity of unplugging the reactor and even during process operation, liquid flow is impeded as solids accumulate. These solids will be a problem and prevention of solid precipitation is highly desirable. This can be effected by increasing the solubility of the heavy oligomers in the liquid hydrocarbon phase by simultaneously recycling some of the lighter oligomer fractions and recycle ethylene to the reaction zone.

INFORMATION DISCLOSURE

U.S. Pat. No. 4,689,437 (Murray) and U.S. Pat. No. 5,523,508 (Krawczyk et al) disclose processes for the oligomerization of ethylene in the presence of a catalyst system containing a transition metal compound, a catalyst activator and an organophosphorus sulfonate ligand in a polar solvent such as sulfolane at preferred operating conditions including a temperature and pressure greater than the critical temperature and pressure of ethylene. These patents fail to disclose the separation of ethylene from the reaction zone effluent and the subsequent recycle of ethylene in accordance with the present invention.

U.S. Pat. No. 2,391,576 (Katz et al) discloses a process for separating hydrocarbon mixtures into a multiplicity of vapor phases.

U.S. Pat. No. 4,795,854 (Levresse) discloses a device for separating a high pressure polyphase mixture of a gas containing liquid particles and particularly a mixture of ethylene and polyethylene which comprises a cylindrical vertical enclosure into which extends an inlet means for supplying the mixture thereto and which is provided at its lower end with an outlet for discharging separated liquids; a vertical cyclone in communication with the enclosure for receiving separated gases therefrom and having an outlet at its upper end for discharging gases separated in the cyclone and a liquid outlet at its lower end for discharging separated liquids therefrom; and an ejector comprising a nozzle, through which the polyphase mixture is fed, a mixing zone connected to the liquid outlet of the cyclone and a diffuser section for reducing the speed of the resultant mixture and being connected to the inlet means for supplying the polyphase mixture to the enclosure.

BRIEF SUMMARY OF THE INVENTION

The purpose of the present invention is the production of linear alpha-olefins from the oligomerization of ethylene using as a catalyst a solution of a transition metal catalyst system in a polar solvent while affording a more economical separation of the unreacted ethylene for recycle to the oligomerization reaction zone. The hydrocarbon phase comprising oligomers and unreacted ethylene is withdrawn from the oligomerization reaction zone and subjected to a physical treatment which tends to render the unreacted ethylene a nonsolvent for oligomers to thereby produce a liquid phase comprising ethylene which may economically be recycled to the oligomerization reaction zone.

One embodiment of the present invention may be characterized as a process for the continuous oligomerization of ethylene to produce linear alpha-olefins comprising: (a) introducing ethylene at oligomerization conditions including a temperature and pressure greater than the critical temperature and pressure of ethylene into a liquid polar phase comprising a solution of transition metal catalyst system in a polar solvent; (b) oligomerizing ethylene in the liquid polar phase to produce oligomers having more than 4 carbon atoms and forming a liquid hydrocarbon phase separate from the liquid polar phase and comprising unreacted ethylene; (c) continually withdrawing and subjecting the liquid hydrocarbon phase to physical treatment which tends to render the ethylene a nonsolvent for oligomers to thereby form a two-phase system with a first liquid phase comprising ethylene in a reduced solvent state and a second liquid phase comprising oligomers; (d) recycling at least a portion of the first liquid phase comprising ethylene produced in step (c) to provide at least a portion of the ethylene in step (a); and (e) recovering the second liquid phase comprising oligomers produced in step (c).

Another embodiment of the present invention may be characterized as a process for the continuous oligomerization of ethylene to produce linear alpha-olefins comprising: (a) introducing ethylene at oligomerization conditions including a temperature and pressure greater than the critical temperature and pressure of ethylene into a liquid polar phase comprising a solution of transition metal catalyst system in a polar solvent; (b) oligomerizing ethylene in the liquid polar phase to produce oligomers having more than 4 carbon atoms and forming a liquid hydrocarbon phase separate from the liquid polar phase and comprising unreacted ethylene; (c) continually withdrawing and subjecting the liquid hydrocarbon phase to physical treatment which tends to render the ethylene a nonsolvent for oligomers to thereby form a two-phase system with a first liquid phase comprising ethylene in a reduced solvent state and a second liquid phase comprising oligomers and ethylene; (d) recycling at least a portion of the first liquid phase comprising ethylene produced in step (c) to provide at least a portion of the ethylene in step (a); (e) fractionating at least a portion of the second liquid phase comprising oligomers and ethylene produced in step (c) to produce a stream comprising ethylene and a stream comprising oligomers; (f) recycling at least a portion of the stream comprising ethylene produced in step (e) to provide at least a portion of the ethylene in step (a); and (g) recovering the stream comprising oligomers produced in step (e).

BRIEF DESCRIPTION OF THE DRAWING

The drawing is a simplified process flow diagram of a preferred embodiment of the present invention. The above-described drawing is intended to be schematically illustrative of the present invention and is not to be a limitation thereof.

DETAILED DESCRIPTION OF THE INVENTION

The present invention is a process for the continuous oligomerization of ethylene to produce linear alpha-olefins. The oligomerization of ethylene using a solution of a transition metal catalyst system in a polar solvent proceeds with the formation of a separate hydrocarbon phase consisting largely of linear alpha-olefins formed according to the Schultz-Flory distribution. At a Schultz-Flory distribution constant of greater than about 0.60 considerable amounts of $C_{20+}$ oligomers are formed which are not completely soluble in the hydrocarbon phase at process temperatures. The oligomerization reaction zone effluent contains unreacted ethylene and up to about 90% of the ethylene can be recovered from the reactor effluent at supercritical conditions and then recycled to the reactor inlet by pumping rather than by compression.

The oligomerization of ethylene is preferably catalyzed by transition metal catalyst systems. A suitable metal catalyst system is described in U.S. Pat. No. 4,689,437 which is incorporated herein. A preferred transition metal catalyst system is a reaction product of three components; a transition metal compound, a catalyst activator and an organophosphorus sulfonate ligand. Since transition metal catalyst systems for ethylene oligomerization are well known in the art, they need not be further discussed herein.

The oligomerization of ethylene is a liquid phase reaction and the catalyst may be either dissolved in a solvent or suspended in a liquid medium. This solvent or liquid medium of course needs to be inert to process components and apparatus under process conditions. Examples of solvents include ethanol, methanol, water, sulfolane (tetramethylenesulfone), ethylene glycol, 1,4-butanediol, ethylene carbonate, as well as mixtures of the foregoing. In the variant under discussion here solvents which permit ready phase separation from oligomer products are preferred in order to have a polar solvent phase and a hydrocarbon phase. The most preferred solvent for ethylene oligomerization is sulfolane in which the catalysts of the present invention are quite soluble but the oligomers are not.

Typical catalyst concentrations are in the range of about 10 ppm to about 1,000 ppm of transition metal. Some of the more active catalysts give quite high reaction rates at 40 ppm, and a broader range of catalyst concentration is between about 0.1 to about 1,000 ppm. In a preferred mode of practicing the present invention catalyst concentrations range between about 15 and about 300 ppm.

In accordance with the present invention, the oligomerization conditions include a temperature in the range of about 40° F. (5° C.) to about 392° F. (200° C.), with the interval between 68° F. (20° C.) and 284° F. (140° C.) preferred and that between 86° F. (30° C.) and about 176° F. (80° C.) even more preferred. Oligomerization pressures preferably are in the range from about 885 psig to about 5,000 psig and more preferably in the range of about 885 to about 2,000 psig. These pressures are the pressures at which the ethylene is introduced into the reactor and at which the reactor is maintained. The critical temperature and pressure of ethylene is 40° F. (5° C.) and 885 psig, respectively, and therefore the oligomer reaction zone is operated at conditions above the critical temperature and pressure of ethylene.

As commented on above, the oligomerization process forms oligomers which are predominantly linear alpha-olefins having from 4 to over 20 carbon atoms and which have low solubility in the polar solvents utilized, especially where sulfolane is the solvent for the transition metal catalyst systems of our invention. Consequently, oligomer formation is accompanied by formation of a separate hydrocarbon phase, at least a portion of which is continually removed. The constituents of this hydrocarbon phase are ethylene oligomers whose relative proportions closely follow a Schultz-Flory distribution. The practice of the present invention is particularly applicable to those cases where substantial amounts of heavy oligomers are formed, which is a function of the Schultz-Flory distribution. By "heavy oligomers" is meant oligomers normally a (waxy) solid at process temperatures, and may be considered as $C_{20+}$ oligomers. These heavy oligomers have a limited, temperature-dependent solubility in the hydrocarbon phase. But since the temperature also affects oligomer product quality via the selectivity to linear alpha-olefins, it is not practical to raise the reaction temperature in order to maintain homogeneity. Unless homogeneity in the hydrocarbon phase is maintained, reactor (or an ancillary unit) clogging results, which is alleviated by the present invention.

The process of the present invention is practiced in a way typical for ethylene oligomerization other than the supercritical recovery of at least a portion of the unreacted ethylene from the reaction zone effluent. Thus, ethylene is continually fed to a reactor sufficient to maintain ethylene pressures between about 885 and about 5000 psig at temperatures between about 5° and about 200° C. The transition metal catalyst system is present in solution in a polar solvent, preferably sulfolane. Oligomerization proceeds with formation of a separate hydrocarbon phase resulting from the low solubility of oligomers in the sulfolane. The hydrocarbon phase containing oligomers and unreacted ethylene is continually removed and subjected to a physical treatment to reduce the solvent ability of the supercritical ethylene.

The reduction of the solvent ability of the supercritical ethylene may be achieved by pressure reduction, temperature increase or a combination thereof. The key to the separation and recycle of the supercritical ethylene is that the capacity of the supercritical ethylene to extract heavier components is highly dependent on its density. As the density of the supercritical ethylene is decreased (by pressure reduction, temperature increase or a combination thereof, the amount of heavier material, i.e., oligomers in this case that can remain in the supercritical ethylene decreases. In accordance with the present invention, it is preferred that the capacity of the supercritical ethylene for oligomers is reduced by both decreasing the pressure and increasing the temperature. It is preferred that the pressure is decreased in the range from about 1350 psig to about 850 psig and that the temperature is increased in the range from about 175° F. (80° C.) to about 400° F. (205° C.). After the reduction of the solvent ability of the supercritical ethylene, the reaction zone effluent is introduced into a supercritical separation zone wherein an overhead liquid stream containing unreacted ethylene is produced, recovered and recycled to the reaction zone. Since the separation of unreacted ethylene from the reactor effluent is not a sharp separation, about 15–25 mol percent of the material recovered and recycled to the reactor is oligomers having up to about 14 carbon atoms. These oligomers which are recycled with the supercritical ethylene are used to aid in solubilizing heavy wax buildup in the oligomerization reaction zone.

A bottoms stream containing oligomers and unreacted ethylene is removed from the supercritical separation zone and subjected to conventional fractionation to recover a stream containing product oligomers and a stream containing unreacted ethylene which is also recycled to the reaction zone.

Detailed Description of the Drawing

The drawing is a preferred embodiment of the present invention and is a simplified flow diagram in which such details as pumps, instrumentation, heat exchange and heat-recovery circuits, compressors and similar hardware have been deleted as being non-essential to the understanding of the techniques involved. The use of such miscellaneous equipment is well within the purview of one skilled in the art of petroleum refining and petrochemical production techniques.

Referring now to the drawing, a fresh feed ethylene stream is introduced into the process via line 1 and is admixed with a first recycle stream containing previously unreacted ethylene and oligomers transported via line 15 and a second recycle stream containing unreacted ethylene transported via line 12. The resulting admixture is introduced by line 2 into oligomerization reaction zone 3 and a resulting product stream containing oligomers and unreacted ethylene is removed from oligomerization reaction zone 3 via line 4 and introduced into heat-exchanger 5. The resulting heated effluent from heat-exchanger 5 is transported via line 6 and introduced into supercritical separation zone 7. An overhead stream containing unreacted ethylene and oligomers is removed from supercritical separation zone 7 via conduit 13 and introduced into heat-exchanger 14. The resulting cooled effluent from heat-exchanger 14 is transported via line 15 and provides the first recycle stream described hereinabove. A bottom stream is removed from supercritical separation zone 7 via line 8 and is introduced into fractionation zone 9. An overhead stream containing unreacted ethylene is removed from the overhead of fractionation zone 9 and transported via line 12 which provides the second recycle stream described hereinabove. A bottom stream containing oligomers is removed from fractionation zone 9 via line 10 and recovered.

The process of the present invention is further demonstrated by the following illustrative embodiment. This illustrative embodiment is, however, not presented to unduly limit the process of this invention, but to further illustrate the advantages of the hereinabove-described embodiment. The following results were not obtained by the actual performance of the present invention but are considered prospective and reasonably illustrative of the expected performance of the invention based upon sound engineering calculations.

Illustrative Embodiment

A fresh feed ethylene stream in an amount of 981 lb mole/hr is introduced into the process and admixed with a first recycle stream from the supercritical separation zone in a total amount of 1154 lb mole/hr with 784 lb mole/hr of ethylene, 213 lb mole/hr butene and the balance (157 lb mole/hr) as heavier oligomers.

A second recycle stream from the oligomer product fractionation zone in an amount of 196 lb mole/hr of ethylene is also recycled and admixed with the fresh feed ethylene and the first recycle stream, and introduced into an oligomerization reaction zone maintained at a temperature of 140° F. and a pressure of 1500 psia. The details of the combined feed stream to the reaction zone and the product stream from the reaction zone are presented in Table 1.

The reaction zone effluent is depressured to a pressure of 1335 psia, heated to 365° F. and introduced into a supercritical separation zone. An overhead liquid stream from the supercritical separation zone is removed and pumped to the oligomerization reaction zone as the first recycle stream. The bottoms stream from the supercritical separation zone is fractionated to produce an overhead stream containing unreacted ethylene in an amount of 196 lb mole/hr which is returned to the oligomerization reaction zone as the second recycle stream. A linear alpha olefin oligomer product stream in an amount of 256 lb mole/hr is recovered from the fractionation zone and has the characteristics presented in Table 1.

The foregoing description and illustrative embodiment clearly illustrate theadvantages encompassed by the method of the present invention and the benefits to be afforded with the use thereof.

TABLE 1

Stream Analysis

|  | Reaction Zone Feed | Reaction Zone Effluent | Linear Alpha Olefin Product Stream |
| --- | --- | --- | --- |
| Ethylene, lb mole | 1961 | 980 | 90 |
| 1-Butene, lb mole | 212 | 303 | 59 |
| 1-Hexene, l mole | 90 | 149 | 38 |
| 1-Octene, lb mole | 38 | 76 | 25 |
| 1-Decene, lb mole | 16 | 41 | 16 |
| 1-Dodecene, ln mole | 7 | 23 | 10 |
| 1-Tetradecene lb, mole | 3 | 14 | 7 |
| 1-Hexadecene, lb mole | 1 | 8 | 4 |
| HEAVIES, lb mole | 3 | 13 | 7 |

What is claimed:

1. A process for the continuous oligomerization of ethylene to produce linear alpha-olefins comprising:

(a) introducing ethylene at oligomerization conditions including a temperature and pressure greater than the critical temperature and pressure of ethylene into a liquid polar phase comprising a solution of transition metal catalyst system in a polar solvent;

(b) oligomerizing ethylene in said liquid polar phase to produce oligomers having more than 4 carbon atoms and forming a liquid hydrocarbon phase separate from said liquid polar phase and comprising unreacted ethylene;

(c) continually withdrawing and subjecting said liquid hydrocarbon phase to physical treatment which tends to render said ethylene a nonsolvent for oligomers to thereby form a two-phase system with a first liquid phase comprising ethylene in a reduced solvent state and a second liquid phase comprising oligomers;

(d) recycling at least a portion of said first liquid phase comprising ethylene produced in step (c) to provide at least a portion of the ethylene in step (a); and (e) recovering said second liquid phase comprising oligomers produced in step (c).

2. The process of claim 1 wherein said transition metal catalyst system comprises a transition metal compound, a catalyst activator and an organophosphorus sulfonate ligand.

3. The process of claim 1 wherein said polar solvent is selected from the group consisting of ethanol, methanol, sulfolane, ethylene glycol, 1,4-butanediol, and ethylene carbonate.

4. The process of claim 1 wherein said polar solvent is sulfolane.

5. The process of claim 1 wherein the oligomerization conditions are from about 5° C. to about 200° C. and a pressure between about 885 psig to about 5,000 psig.

6. The process of claim 1 wherein said reduced solvent state in step (c) includes a pressure in the range from about 850 to about 1350 psig and a temperature in the range from about 175 to about 400° F.

7. A process for the continuous oligomerization of ethylene to produce linear alpha-olefins comprising:

(a) introducing ethylene at oligomerization conditions including a temperature and pressure greater than the critical temperature and pressure of ethylene into a liquid polar phase comprising a solution of transition metal catalyst system in a polar solvent;

(b) oligomerizing ethylene in said liquid polar phase to produce oligomers having more than 4 carbon atoms and forming a liquid hydrocarbon phase separate from said liquid polar phase and comprising unreacted ethylene;

(c) continually withdrawing and subjecting said liquid hydrocarbon phase to physical treatment which tends to render said ethylene a nonsolvent for oligomers to thereby form a two-phase system with a first liquid phase comprising ethylene in a reduced solvent state and a second liquid phase comprising oligomers and ethylene;

(d) recycling at least a portion of said first liquid phase comprising ethylene produced in step (c) to provide at least a portion of the ethylene in step (a);

(e) fractionating at least a portion of said second liquid phase comprising oligomers and ethylene produced in step (c) to produce a stream comprising ethylene and a stream comprising oligomers;

(f) recycling at least a portion of said stream comprising ethylene produced in step (e) to provide at least a portion of the ethylene in step (a); and (g) recovering said stream comprising oligomers produced in step (e).

8. The process of claim 7 wherein said transition metal catalyst system comprises a transition metal compound, a catalyst activator and an organophosphorus sulfonate ligand.

9. The process of claim 7 wherein said polar solvent is selected from the group consisting of ethanol, methanol, sulfolane, ethylene glycol, 1,4-butanediol, and ethylene carbonate.

10. The process of claim 7 wherein said polar solvent is sulfolane.

11. The process of claim 7 wherein the oligomerization conditions are from about 5° C. to about 200° C. and a pressure between about 885 psig to about 5,000 psig.

12. The process of claim 7 wherein said reduced solvent state in step (c) includes a pressure in the range from about 850 to about 1350 psig and a temperature in the range from about 175 to about 400° F.

* * * * *